United States Patent
May et al.

(10) Patent No.: US 12,163,513 B2
(45) Date of Patent: *Dec. 10, 2024

(54) MEMBRANE PUMP USAGE CONDITION DETECTION

(71) Applicant: QUANTA DIALYSIS TECHNOLOGIES, LTD., Warwickshire (GB)

(72) Inventors: Paul Edward May, Warwicksire (GB); Chung Chan Tham, Warwickshire (GB); Lewis Reading, Warwickshire (GB); Clive Henry Buckberry, Warwicksire (GB); Eduardo Esser, Warwicksire (GB)

(73) Assignee: QUANTA DIALYSIS TECHNOLOGIES LTD., Warwickshire (GB)

( * ) Notice: Subject to any disclaimer, the term of this patent is extended or adjusted under 35 U.S.C. 154(b) by 1303 days.

This patent is subject to a terminal disclaimer.

(21) Appl. No.: 16/077,170

(22) PCT Filed: Jan. 31, 2017

(86) PCT No.: PCT/GB2017/050235
§ 371 (c)(1),
(2) Date: Aug. 10, 2018

(87) PCT Pub. No.: WO2017/137723
PCT Pub. Date: Aug. 17, 2017

(65) Prior Publication Data
US 2019/0024654 A1     Jan. 24, 2019

(30) Foreign Application Priority Data

Feb. 10, 2016 (GB) ...................... 1602391

(51) Int. Cl.
*F04B 49/06* (2006.01)
*A61M 1/14* (2006.01)
(Continued)

(52) U.S. Cl.
CPC ......... *F04B 49/065* (2013.01); *A61M 1/1524* (2022.05); *A61M 1/154* (2022.05);
(Continued)

(58) Field of Classification Search
None
See application file for complete search history.

(56) References Cited

U.S. PATENT DOCUMENTS 2,696,173 A   12/1954   Thormod
3,338,171 A    8/1967   Conklin et al.
(Continued)

FOREIGN PATENT DOCUMENTS

CA            81430        8/1997
DE         10024447 A1    11/2001
(Continued)

OTHER PUBLICATIONS

International Search Report and Written Opinon issued for International Application No. PCT/GB2017/050235, dated Apr. 10, 2017.
(Continued)

*Primary Examiner* — Hayden Brewster
(74) *Attorney, Agent, or Firm* — The Marbury Law Group, PLLC

(57) ABSTRACT

A membrane pump usage condition detection system and a method of determining a membrane pump usage condition. The membrane pump usage condition detection system comprises a membrane pump defining a flow path arranged to be opened and closed by at least one valve, a measuring device; a comparator; and a signal generator. The measuring
(Continued)

device is configured to determine an electrical characteristic between two points on the flow path of the membrane pump, one point arranged upstream of the at least one valve and the other point arranged downstream of the at least one valve. The measuring device measures the electrical characteristic when the at least one valve is closed. The comparator is configured to monitor the electrical characteristic. The signal generator is arranged to provide an output signal when the electrical characteristic is indicative of a membrane pump usage condition.

17 Claims, 6 Drawing Sheets

(51) Int. Cl.
  *A61M 1/16* (2006.01)
  *A61M 60/113* (2021.01)
  *A61M 60/268* (2021.01)
  *A61M 60/427* (2021.01)
  *A61M 60/515* (2021.01)
  *A61M 60/538* (2021.01)
  *F04B 43/04* (2006.01)
  *F04B 43/06* (2006.01)
  *F04B 49/10* (2006.01)
  *F04B 49/22* (2006.01)

(52) U.S. Cl.
  CPC .......... *A61M 1/155* (2022.05); *A61M 1/1561* (2022.05); *A61M 1/1565* (2022.05); *A61M 1/1605* (2014.02); *A61M 60/113* (2021.01); *A61M 60/268* (2021.01); *A61M 60/427* (2021.01); *A61M 60/515* (2021.01); *A61M 60/538* (2021.01); *F04B 43/043* (2013.01); *F04B 43/06* (2013.01); *F04B 49/106* (2013.01); *F04B 49/22* (2013.01); *F04B 2201/0605* (2013.01)

(56) References Cited

U.S. PATENT DOCUMENTS

| | | |
|---|---|---|
| 3,468,261 A | 9/1969 | Schmierer |
| 3,605,566 A | 9/1971 | Vetter |
| 3,606,592 A | 9/1971 | Madurski et al. |
| 3,753,493 A | 8/1973 | Mellor |
| 3,774,762 A | 11/1973 | Lichtenstein |
| 3,807,906 A | 4/1974 | Breit |
| 3,921,622 A | 11/1975 | Cole |
| 3,972,320 A | 8/1976 | Kalman |
| 4,070,725 A | 1/1978 | Cornelius |
| 4,142,845 A | 3/1979 | Lepp et al. |
| 4,161,264 A | 7/1979 | Malmgren |
| 4,205,686 A | 6/1980 | Harris et al. |
| 4,353,990 A | 10/1982 | Manske et al. |
| 4,366,061 A | 12/1982 | Papanek et al. |
| 4,368,261 A | 1/1983 | Klose et al. |
| 4,370,983 A | 2/1983 | Lichtenstein |
| 4,430,048 A | 2/1984 | Fritsch |
| 4,494,912 A | 1/1985 | Pauliukonis |
| D277,991 S | 3/1985 | Becker |
| 4,534,755 A | 8/1985 | Calvert et al. |
| 4,534,756 A | 8/1985 | Nelson |
| 4,546,669 A | 10/1985 | Fischer et al. |
| 4,564,342 A | 1/1986 | Weber et al. |
| 4,599,165 A | 7/1986 | Chevallet |
| 4,648,869 A | 3/1987 | Bobo, Jr. |
| 4,666,598 A | 5/1987 | Heath et al. |
| 4,710,163 A | 12/1987 | Butterfield |
| 4,771,792 A | 9/1988 | Seale |
| 4,828,543 A | 5/1989 | Weiss et al. |
| 4,897,184 A | 1/1990 | Shouldice et al. |
| D308,249 S | 5/1990 | Buckley |
| 4,969,991 A | 11/1990 | Valadez |
| 5,000,664 A | 3/1991 | Lawless et al. |
| 5,012,197 A | 4/1991 | Seiffert et al. |
| 5,032,265 A | 7/1991 | Jha et al. |
| 5,055,198 A | 10/1991 | Shettigar |
| 5,095,910 A | 3/1992 | Powers |
| 5,103,211 A | 4/1992 | Daoud et al. |
| 5,126,831 A | 6/1992 | Nakagawara |
| 5,232,434 A | 8/1993 | Inagaki et al. |
| 5,252,213 A | 10/1993 | Ahmad et al. |
| D341,890 S | 11/1993 | Sievert et al. |
| D344,339 S | 2/1994 | Yoshikawa et al. |
| 5,304,349 A | 4/1994 | Polaschegg |
| D347,896 S | 6/1994 | Dickinson et al. |
| D351,470 S | 10/1994 | Scherer et al. |
| 5,385,540 A | 1/1995 | Abbott et al. |
| 5,421,823 A | 6/1995 | Kamen et al. |
| 5,458,468 A | 10/1995 | Ye et al. |
| 5,476,368 A | 12/1995 | Rabenau et al. |
| 5,476,792 A | 12/1995 | Ezrielev et al. |
| D370,979 S | 6/1996 | Pascale et al. |
| 5,558,347 A | 9/1996 | Nicholson |
| 5,586,872 A | 12/1996 | Skobelev et al. |
| 5,586,873 A | 12/1996 | Novak et al. |
| 5,591,344 A | 1/1997 | Kenley et al. |
| 5,643,201 A | 7/1997 | Peabody et al. |
| 5,650,071 A | 7/1997 | Brugger et al. |
| 5,653,456 A | 8/1997 | Mough |
| 5,658,456 A | 8/1997 | Kenley et al. |
| 5,665,307 A | 9/1997 | Kirschner et al. |
| 5,727,550 A | 3/1998 | Montecalvo |
| D395,085 S | 6/1998 | Kenley et al. |
| 5,788,851 A | 8/1998 | Kenley et al. |
| 5,807,322 A | 9/1998 | Lindsey et al. |
| 5,882,300 A | 3/1999 | Malinouskas et al. |
| 5,948,247 A | 9/1999 | Gillerfalk et al. |
| 5,957,670 A | 9/1999 | Duncan et al. |
| 5,995,910 A | 11/1999 | Discenzo |
| 6,077,443 A | 6/2000 | Goldau |
| 6,126,831 A | 10/2000 | Goldau et al. |
| 6,132,378 A | 10/2000 | Marino |
| 6,143,181 A | 11/2000 | Falkvall et al. |
| 6,153,102 A | 11/2000 | Kenley et al. |
| 6,216,029 B1 | 4/2001 | Paltieli |
| 6,218,329 B1 | 4/2001 | Singh et al. |
| 6,251,279 B1 | 6/2001 | Peterson et al. |
| 6,261,065 B1 | 7/2001 | Nayak et al. |
| 6,303,036 B1 | 10/2001 | Collins et al. |
| 6,382,923 B1 | 5/2002 | Gray |
| 6,514,462 B1 | 2/2003 | Simons |
| 6,558,347 B1 | 5/2003 | Jhuboo et al. |
| 6,582,206 B2 | 6/2003 | Schluecker |
| 6,626,832 B1 | 9/2003 | Paltieli et al. |
| 6,626,878 B1 | 9/2003 | Leisner et al. |
| 6,645,176 B1 | 11/2003 | Christenson et al. |
| 6,663,829 B1 | 12/2003 | Kjellstrand |
| 6,733,476 B2 | 5/2004 | Christenson et al. |
| 6,743,204 B2 | 6/2004 | Christenson et al. |
| 6,801,646 B1 | 10/2004 | Pena et al. |
| 6,814,547 B2 | 11/2004 | Childers et al. |
| 6,967,002 B1 | 11/2005 | Edgson et al. |
| 7,040,142 B2 | 5/2006 | Burbank |
| 7,107,837 B2 * | 9/2006 | Lauman .............. A61M 1/1658 73/232 |
| 7,153,286 B2 | 12/2006 | Busby et al. |
| 7,220,358 B2 | 5/2007 | Schacht et al. |
| 7,284,964 B2 | 10/2007 | McDowell et al. |
| 7,383,721 B2 * | 6/2008 | Parsons .................... E03D 3/02 73/46 |
| 7,434,312 B2 | 10/2008 | Christenson et al. |
| 7,494,590 B2 | 2/2009 | Felding et al. |
| 7,604,398 B1 | 10/2009 | Akers et al. |
| 7,648,627 B2 | 1/2010 | Beden et al. |
| 7,857,976 B2 | 12/2010 | Bissler et al. |
| 7,874,999 B2 | 1/2011 | Busby |
| 7,896,197 B2 | 3/2011 | Furey et al. |
| D641,882 S | 7/2011 | Hickey et al. |
| 8,114,043 B2 | 2/2012 | Muller |

(56) References Cited

U.S. PATENT DOCUMENTS

| | | |
|---|---|---|
| 8,132,388 B2 | 3/2012 | Nagy et al. |
| 8,137,184 B2 | 3/2012 | Ajiro et al. |
| 8,137,300 B2 | 3/2012 | Han et al. |
| 8,167,431 B2 | 5/2012 | DeCusatis et al. |
| 8,187,184 B2 | 5/2012 | Muller et al. |
| 8,192,388 B2 | 6/2012 | Hogard |
| 8,197,431 B2 | 6/2012 | Bennison |
| 8,221,320 B2 | 7/2012 | Bouton |
| 8,348,850 B2 | 1/2013 | Frinak et al. |
| 8,360,977 B2 | 1/2013 | Marttila et al. |
| 8,529,490 B2 | 9/2013 | Wariar et al. |
| 8,535,522 B2 | 9/2013 | Fulkerson et al. |
| 8,535,525 B2 | 9/2013 | Heyes et al. |
| D693,469 S | 11/2013 | Chung et al. |
| 8,597,505 B2 | 12/2013 | Fulkerson et al. |
| D702,842 S | 4/2014 | Hyde et al. |
| 8,685,244 B2 | 4/2014 | Heyes et al. |
| 8,696,571 B2 | 4/2014 | Marttila et al. |
| 8,708,908 B2 | 4/2014 | Bouton |
| 8,708,946 B2 | 4/2014 | Han et al. |
| D705,432 S | 5/2014 | Lura et al. |
| 8,798,908 B2 | 8/2014 | Bourdeaut |
| 8,801,646 B2 | 8/2014 | Han et al. |
| D714,454 S | 9/2014 | Amemiya et al. |
| D714,946 S | 10/2014 | Lura et al. |
| 8,926,544 B2 | 1/2015 | Hogard et al. |
| D724,740 S | 3/2015 | Collins et al. |
| 8,974,394 B2 | 3/2015 | Frinak et al. |
| 9,011,334 B2 | 4/2015 | Bouton |
| D735,868 S | 8/2015 | Mareguddi et al. |
| 9,220,825 B2 * | 12/2015 | Buckberry ............ A61M 60/40 |
| D781,410 S | 3/2017 | Ritter et al. |
| 9,744,285 B2 | 8/2017 | Heyes et al. |
| 9,833,553 B2 * | 12/2017 | Higgitt ................ A61M 1/1641 |
| 10,314,962 B2 | 6/2019 | Buckberry |
| 10,456,516 B2 | 10/2019 | Heyes et al. |
| D867,597 S | 11/2019 | Bauer et al. |
| 10,543,305 B2 | 1/2020 | Buckberry et al. |
| D879,967 S | 3/2020 | Verguidi et al. |
| D907,211 S | 1/2021 | Spurling |
| 10,881,775 B2 | 1/2021 | Wallace |
| 10,960,120 B2 * | 3/2021 | Wallace ................ A61M 1/16 |
| D924,410 S | 7/2021 | Mendoza et al. |
| D938,046 S | 12/2021 | Gupta et al. |
| 11,365,728 B2 | 6/2022 | Westenbrink |
| 11,571,499 B2 | 2/2023 | Milad et al. |
| 11,583,618 B2 | 2/2023 | Buckberry et al. |
| 2003/0217962 A1 | 11/2003 | Childers et al. |
| 2004/0195157 A1 | 10/2004 | Mullins et al. |
| 2004/0206703 A1 | 10/2004 | Bosetto et al. |
| 2004/0215129 A1 | 10/2004 | Edgson et al. |
| 2004/0223857 A1 | 11/2004 | Kline |
| 2005/0020961 A1 | 1/2005 | Burbank et al. |
| 2005/0205476 A1 | 9/2005 | Chevallet et al. |
| 2005/0209547 A1 | 9/2005 | Burbank et al. |
| 2005/0234384 A1 | 10/2005 | Westberg |
| 2006/0121623 A1 | 6/2006 | He et al. |
| 2007/0083193 A1 | 4/2007 | Werneth et al. |
| 2008/0006089 A1 * | 1/2008 | Adnan .................... G01B 5/00 |
| | | 417/63 |
| 2008/0200865 A1 | 8/2008 | Bedingfield |
| 2008/0283096 A1 | 11/2008 | Scheringer et al. |
| 2009/0007642 A1 | 1/2009 | Busby et al. |
| 2009/0009290 A1 | 1/2009 | Kneip et al. |
| 2009/0012450 A1 | 1/2009 | Shah et al. |
| 2009/0012452 A1 | 1/2009 | Slepicka et al. |
| 2009/0012457 A1 | 1/2009 | Childers et al. |
| 2009/0101550 A1 | 4/2009 | Muller et al. |
| 2009/0211975 A1 | 8/2009 | Brugger et al. |
| 2009/0230043 A1 | 9/2009 | Heyes et al. |
| 2010/0043694 A1 | 2/2010 | Patel |
| 2010/0045471 A1 | 2/2010 | Meyers |
| 2010/0089807 A1 | 4/2010 | Heyes et al. |
| 2010/0139254 A1 | 6/2010 | Sebestyen et al. |
| 2010/0263687 A1 | 10/2010 | Braun et al. |
| 2011/0009797 A1 | 1/2011 | Kelly et al. |
| 2011/0034850 A1 | 2/2011 | Jonsson |
| 2011/0132838 A1 | 6/2011 | Curtis et al. |
| 2011/0168614 A1 | 7/2011 | Pouchoulin et al. |
| 2012/0164022 A1 | 6/2012 | Muginstein et al. |
| 2012/0269907 A1 | 10/2012 | Coates |
| 2012/0276549 A1 | 11/2012 | Cunningham et al. |
| 2012/0292237 A1 | 11/2012 | Heyes et al. |
| 2012/0308431 A1 | 12/2012 | Kotsos et al. |
| 2013/0037465 A1 | 2/2013 | Heyes et al. |
| 2013/0056419 A1 | 3/2013 | Curtis |
| 2013/0153495 A1 | 6/2013 | Kelly et al. |
| 2013/0199998 A1 | 8/2013 | Kelly et al. |
| 2013/0274642 A1 | 10/2013 | Soykan et al. |
| 2014/0224736 A1 | 8/2014 | Heide |
| 2014/0251885 A1 | 9/2014 | Heyes |
| 2014/0271106 A1 * | 9/2014 | Alessandro ......... F04D 27/0261 |
| | | 415/118 |
| 2014/0299544 A1 | 10/2014 | Wilt et al. |
| 2015/0027951 A1 * | 1/2015 | Wallace ............... A61M 1/1635 |
| | | 210/646 |
| 2015/0076053 A1 * | 3/2015 | Higgitt ................ A61M 1/1641 |
| | | 210/321.71 |
| 2015/0112119 A1 * | 4/2015 | Buckberry .......... A61M 60/892 |
| | | 600/16 |
| 2015/0129481 A1 | 5/2015 | Higgitt et al. |
| 2015/0238673 A1 | 8/2015 | Gerber et al. |
| 2015/0258263 A1 * | 9/2015 | Hogard ................. A61M 1/342 |
| | | 210/103 |
| 2015/0352269 A1 | 12/2015 | Gerber et al. |
| 2015/0359954 A1 | 12/2015 | Gerber et al. |
| 2016/0045656 A1 | 2/2016 | Buckberry |
| 2016/0051743 A1 | 2/2016 | Buckberry |
| 2016/0058933 A1 | 3/2016 | Ballantyne et al. |
| 2016/0076535 A1 * | 3/2016 | Clifton .................. F04B 49/065 |
| | | 73/168 |
| 2016/0077644 A1 | 3/2016 | Ritter et al. |
| 2016/0199558 A1 | 7/2016 | Buckberry |
| 2017/0056576 A1 | 3/2017 | Doyle et al. |
| 2017/0167983 A1 | 6/2017 | Klomp et al. |
| 2017/0252498 A1 | 9/2017 | Heyes et al. |
| 2017/0296730 A1 | 10/2017 | Soto et al. |
| 2018/0133391 A1 | 5/2018 | Heyes et al. |
| 2018/0154059 A1 | 6/2018 | Heyes et al. |
| 2018/0193545 A1 | 7/2018 | Crnkovich et al. |
| 2018/0344915 A1 | 12/2018 | Wallace |
| 2019/0001042 A1 | 1/2019 | Buckberry |
| 2019/0015577 A1 | 1/2019 | Garrido et al. |
| 2019/0024654 A1 * | 1/2019 | May .................... A61M 60/268 |
| 2019/0358381 A1 * | 11/2019 | Westenbrink ........... F04B 51/00 |
| 2019/0374698 A1 | 12/2019 | Buckberry et al. |
| 2019/0376504 A1 | 12/2019 | Westenbrink |
| 2019/0385434 A1 | 12/2019 | Yuds et al. |
| 2020/0030515 A1 | 1/2020 | Merchant |
| 2020/0075159 A1 | 3/2020 | Bardorz et al. |
| 2020/0268958 A1 | 8/2020 | Heyes et al. |
| 2020/0276372 A1 | 9/2020 | Milad et al. |
| 2020/0330671 A1 | 10/2020 | Buckberry et al. |
| 2021/0110920 A1 | 4/2021 | Heyes et al. |
| 2022/0001087 A1 | 1/2022 | Heyes et al. |
| 2022/0160943 A9 | 5/2022 | Buckberry et al. |
| 2022/0241480 A1 | 8/2022 | Fincham |
| 2022/0241573 A1 | 8/2022 | Fincham |

FOREIGN PATENT DOCUMENTS

| | | |
|---|---|---|
| EA | 004375764-0001 | 10/2017 |
| EA | 004375764-0002 | 10/2017 |
| EA | 007955125-0002 | 6/2020 |
| EP | 0165751 A2 | 12/1985 |
| EP | 0754468 A2 | 1/1997 |
| EP | 2219703 A1 | 8/2010 |
| EP | 2955512 A1 | 12/2015 |
| FR | 2 310 136 | 12/1976 |
| GB | 9007955125-0001 | 5/2020 |
| GB | 9007955125-0002 | 5/2020 |
| JP | H04266740 | 2/1991 |
| JP | H06261872 | 9/1994 |

(56) References Cited

FOREIGN PATENT DOCUMENTS

| | | | |
|---|---|---|---|
| JP | H06261872 A * | 9/1994 | ............. A61B 5/026 |
| JP | H07174659 A * | 7/1995 | ............. G01M 3/04 |
| JP | 2000130334 | 5/2000 | |
| JP | D1645323 | 11/2020 | |
| WO | WO 81/01800 | 7/1981 | |
| WO | WO 91/00113 | 1/1991 | |
| WO | WO 91/16542 | 10/1991 | |
| WO | 1995006205 | 3/1995 | |
| WO | WO 95/25893 | 9/1995 | |
| WO | WO 96/25214 | 8/1996 | |
| WO | WO 97/10013 | 3/1997 | |
| WO | WO 97/28368 | 8/1997 | |
| WO | WO 99/29356 | 6/1999 | |
| WO | WO 2000/006217 | 2/2000 | |
| WO | WO 00/57935 | 10/2000 | |
| WO | WO 02/066833 | 8/2002 | |
| WO | WO 02/081917 | 10/2002 | |
| WO | WO 2003/101510 | 12/2003 | |
| WO | WO 2005/044339 | 5/2005 | |
| WO | WO 2005/080794 | 9/2005 | |
| WO | WO 2006/120415 | 11/2006 | |
| WO | WO 2006/120417 | 11/2006 | |
| WO | WO 2008/100671 | 8/2008 | |
| WO | WO 2008/106191 | 9/2008 | |
| WO | WO 2008/135245 | 11/2008 | |
| WO | WO 2009/006489 | 1/2009 | |
| WO | WO 2009/024333 | 2/2009 | |
| WO | WO 2009/038834 | 3/2009 | |
| WO | WO 2009/061608 | 5/2009 | |
| WO | WO 2009/127624 | 10/2009 | |
| WO | WO 2010/089130 | 8/2010 | |
| WO | WO 2010/146343 | 12/2010 | |
| WO | WO 2011/027118 | 3/2011 | |
| WO | WO 2011/068885 | 6/2011 | |
| WO | WO 2011/105697 | 9/2011 | |
| WO | WO 2011/105698 | 9/2011 | |
| WO | WO 2013/052680 | 4/2013 | |
| WO | WO 2013/057109 | 4/2013 | |
| WO | WO 2013/110906 | 8/2013 | |
| WO | WO 2013/110919 | 8/2013 | |
| WO | WO 2013/114063 | 8/2013 | |
| WO | WO 2013/121162 | 8/2013 | |
| WO | WO-2013110906 A1 * | 8/2013 | ............. A61M 1/16 |
| WO | WO-2013110919 A1 * | 8/2013 | ............. A61M 1/16 |
| WO | WO-2013121163 A1 * | 8/2013 | ............. A61M 60/40 |
| WO | WO 2014/072195 | 5/2014 | |
| WO | WO 2014/082855 | 6/2014 | |
| WO | WO 2014/155121 | 10/2014 | |
| WO | WO 2015/007596 | 1/2015 | |
| WO | WO 2015/022537 | 2/2015 | |
| WO | WO 2016/016870 | 2/2016 | |
| WO | WO-2017137723 A1 * | 8/2017 | ............. A61M 1/1601 |
| WO | WO-2018115816 A1 * | 6/2018 | ............. A61M 1/367 |

OTHER PUBLICATIONS

Search Report issued for GB1602391.3, dated Sep. 16, 2016.

Ergo-Express Motorized Dialysis Cart, Aug. 14, 2017, youtube.com [online], [site visited Jan. 9, 2022], Available from internet, URL: <https://www.youtube.com/watch?v=j4rAXthOmbY> (Year: 2017).

He et al., "A Fluorescent Sensor with High Selectivity and Sensitivity for Potassium in Water," Journal of the American Chemical Society 2003 125 (6), 1468-1469.

Home Dialysis Tescon Aqua Tech, Aug. 1, 2020, youtube.com [online], [site visited Jan. 9, 2022], Available from internet, URL: <https://www.youtube.com/watch?v=WLLPZoS_mz4> (Year: 2020).

Kivi, Air Embolism, Healthline, Aug. 20, 2012, p. 1-5.

LHO2028 Portable Hemodialysis Machine, date unknown, aliexpress.com [online], [site visited Jan. 4, 2022], Available from internet: <https://www.aliexpress.com/item/1005003324875329.html?randl_currency=USD&_randl_shipto=US&src=google&afffcid=1003bab3b8db4e93b9ba88522a14cfc1-1641319351626-05232-UneMJZVf&aff_fsk=UneMJZVf&aff_platform=aaf&sk=UneMJZVf&aff_trace_key= (Year: 2022).

Medical Hemodialysis Machine, date unknown, aliexpress.com [online], [site visited Jan. 4, 2022], Available from internet: <https://www.aliexpress.com/item/1005003445721549.html?_randl_currency=USD&_randl_shipto=US&src=google&aff_fcid=a524f3f9cd9b4976b6b47962f3439d62-1641319166409-02691-UneMJZVf&aff_fsk=UneMJZVf&aff_platform=aaf&sk=UneMJZVf&aff_trace_key=a524f3f9cd9b4976b6b47962f3439d62-1641319166409-02691-UneMJZVf&terminal_id=d0c2cca4b7664d128cb4801a9ef03ff2> (Year: 2022).

Millenium HX Portable Dialysis Water System, Jul. 2, 2014, youtube.com [online], [site visited Jan. 10, 2022], Available from internet, URL: <https://www.youtube.com/watch?v=IGEbPi2CDsw> (Year: 2014).

Portable home dialysis device, Nov. 2, 2017, med-technews.com [online], [site visited Jan. 4, 2022], Available from internet: <https://www.med-technews.com/news/portable-home-dialysis-device-to-launch-next-year/ (Year: 2017).

European Patent Office, "International Preliminary Report on Patentability," issued in International Patent Application No. PCT/GB2017/053738, dated Jun. 25, 2019 (8 pages).

European Patent Office, "International Preliminary Report and Written Opinion," issued in International Patent Application No. PCT/GB2017/053738, dated Feb. 27, 2018 (11 pages).

* cited by examiner

MEMBRANE PUMP USAGE CONDITION DETECTION

This application is a National Stage Entry entitled to and hereby claiming priority under 35 U.S.C. §§ 365 and 371 to corresponding PCT Application No. PCT/GB2017/050235, filed Jan. 31, 2017 entitled "Membrane Pump Usage Condition Detection", which in turn claims priority to G.B. Patent Application No.: 1602391.3, filed Feb. 10, 2016, entitled the same. The disclosures of the above applications are incorporated herein by reference in their entireties.

The present invention relates to a membrane pump usage condition detection system and a method of determining a membrane pump usage condition.

Fluid pumps, for example blood pumps for the extracorporeal circulation of blood are used in a number of medical applications, for example in hemodialysis, and haemodiafiltration.

In hemodialysis machines, it is known to use a disposable cartridge comprising a rigid frame defining fluid pathways and chambers and a flexible membrane covering a surface of the cartridge. The cartridge is loaded into a hemodialysis machine, where pressure, typically pneumatic pressure, exerted on the outside surface of the flexible membrane, causes the membrane to move back and forth. This back and forth action in the region of a chamber acts as a fluid pump, which is thus often referred to as a membrane pump. Such a machine is disclosed in WO 2013/121163, the contents thereof are hereby incorporated by reference.

The movement may also be used to mix two or more fluids in a chamber, such as bicarbonate and acid to create dialysate.

The movement of the flexible membrane may also be used to open and close valves defined in the rigid frame of the disposable cartridge. Such a system is disclosed in WO 2013/110919, the contents thereof are hereby incorporated by reference.

Because of its use in hemodialysis, in pumping and mixing fluids, the cartridge may be referred to as a haemodialysis pulsatile pumping cartridge. Such a disposable cartridge is typically made of a rigid frame of polyethylene and a flexible membrane of polyvinyl chloride (PVC).

In use, the disposable cartridge is loaded in a hemodialysis machine and undergoes repeated deformations in the localised regions of the pump chambers, mixing chambers and valves. In a typical cycle, the machine will perform a priming stage, a treatment stage, including flow balance and ultrafiltration stages following by a purge stage.

Such a dialysis machine relies on volumetric control. Dosing and mixing of fluids is controlled by the volume of the pump chambers which in turn is affected by the flexibility of the membrane. The specific flexibility of the membrane is therefore essential to the accurate running of the dialysis machine. Similarly, flow of fluids into and out of the pump chambers is controlled by inlet and outlet valves which rely on the deformation of the flexible membrane.

Repeated deformations gradually cause plastic deformation of the flexible membrane. Thus the disposable cartridges may be engineered to withstand a specific cycle loading, along with a reserve factor. Once used, the disposable cartridge is disposed of and should not be used again.

Re-use of a cartridge designed for a single cycle, or re-use of a cartridge designed for a specific number of cycles, beyond that number of cycles, may reduce the efficacy of treatment and has the potential to cause damage to the dialysis machine.

Given the typical make-up of the disposable cartridge, and that a typical cycle ends with a purge stage that washes and empties the cartridge to remove any residual fluids, a used cartridge does not visibly show any distinct features, as compared to an unused cartridge. Therefore there is a risk of cartridge re-use, either deliberate or accidental.

Valve leak systems are installed in the dialysis machine to detect if any of the valves on the dialysis cartridge are not closing properly, such that there is a leak of fluid through the valve. The valve leak system comprises first and second conductivity electrodes arranged upstream and downstream of the valve respectively. A conductivity measurement is taken across the electrodes when the valve is closed. For a normally functioning valve, a low conductivity, or indeed no conductivity should be detected when the valve is closed. If a valve is leaking however, a high conductivity is detected, as the leaking fluid carries the charge through the valve, between the first and second conductivity electrodes.

The present invention aims to provide a membrane pump usage condition detection system and a method of determining a membrane pump usage condition and that mitigates one or more of the above problems.

According to a first aspect of the present invention, there is provided a membrane pump usage condition detection system comprising a membrane pump defining a flow path arranged to be opened and closed by at least one valve, a measuring device, a comparator and a signal generator, wherein the measuring device is configured to determine an electrical characteristic between two points on the flow path of the membrane pump, one point arranged upstream of the at least one valve and the other point arranged downstream of the at least one valve, whereby the measuring device measures the electrical characteristic when the at least one valve is closed, and wherein the comparator is configured to monitor the electrical characteristic; and the signal generator is arranged to provide an output signal when the electrical characteristic is indicative of a membrane pump usage condition.

Thus the system provides an output signal characterising the membrane pump usage condition using data from a valve leak system. This may give an operator of a cartridge incorporating the membrane pump, information concerning the overall condition of the cartridge. As data from the valve leak system is used, the membrane pump usage condition detection system requires no additional hardware.

The electrical characteristic may be one of conductance, impedance or capacitance or any other electrical characteristic measurable across the valve.

The detection system may further comprise a processor arranged to receive the output signal. The output signal may be stored in the processor. Thus further analysis may be performed on the identified characteristic. Patterns of deliberate or accidental cartridge re-use may then be monitored.

The membrane pump may be provided on a cartridge. The membrane pump usage condition may be indicative of a cartridge usage condition.

The processor may calculate the specific number of cartridge uses from the electrical characteristic indicative of the membrane pump usage condition.

The output signal may be an error message preventing further cartridge use. This prevents deliberate or accidental cartridge re-use, or re-use of a cartridge beyond a specified number of uses. This may be notified to the user/operator of the dialysis machine in the form of an audible or visual alarm.

The comparator may compare the electrical characteristic with a pre-determined threshold value. Alternatively, the comparator may compare the electrical characteristic with a dynamic threshold value.

The output signal may be provided when the electrical characteristic is above the threshold value. Alternatively, the output signal is provided when the electrical characteristic falls below the threshold value.

The output signal may be an alarm indicating a net fluid removal error. A valve leak could cause net fluid removal error by not fully filing up or emptying the pump with dialysate. Hence, when a valve leak is detected by measuring the frequency an alarm is generated to stop treatment.

The processor may be programmed to permit a set number of cartridge re-uses.

The measuring device may be a pair of electrodes. Alternatively the measuring device may be a pair of capacitance probes.

According to a second aspect of the present invention, there is provided a method of determining a membrane pump usage condition comprising the steps of: providing a dialysis machine including a cartridge having a deformable membrane, the cartridge and deformable membrane together defining a membrane pump, the membrane pump defining a flow path arranged to be opened and closed by at least one valve, a measuring device, a comparator; and a signal generator, configuring the measuring device for determining an electrical characteristic between two points on the flow path of the membrane pump, one point arranged upstream of the at least one valve and the other point arranged downstream of the at least one valve, operating the dialysis machine through a cycle, measuring the electrical characteristic whenever the at least one valve is closed, monitoring the electrical characteristic throughout the cycle using the comparator, providing an output signal when the electrical characteristic is indicative of a membrane pump usage condition.

Thus the method of the present invention provides a measure of cartridge deterioration (and re-use) using the data output of the existing valve leak detection system.

The electrical characteristic may be one of conductance, impedance or capacitance. The cycle may include at least one of a priming stage, a treatment stage, and a purge stage.

The membrane pump usage condition may be indicative of a cartridge usage condition.

The step of determining the membrane pump usage condition includes recording a characteristic value above a limit value. Alternatively, the step of determining the membrane pump usage condition may include recording a series of characteristic values above a limit value.

The characteristic value may be a decay rate of the valve leak frequency following a spike in the valve leak frequency. The characteristic values are observed in the data of the valve leak detection system. The so-called background levels change with cartridge re-use. The background level of the valve leak detection system is observed to spike to higher levels during cartridge re-use. The background level of the valve leak detection system is observed to spike to higher levels and then more rapidly decay during cartridge re-use.

The decay rate of the valve leak frequency following a spike in the valve leak frequency may be indicative of a specific number of cartridge uses. Thus the specific number of cartridge uses may be determined.

The characteristic value may be the mean, median or modal average valve leak frequency during the cycle. This value may be compared to a signature value for a specific cartridge, providing an indication of the level of cartridge re-use.

The cartridge usage condition may be determined using a processor provided on the dialysis machine.

The valve leak frequency may be recorded at a sample rate of 1 sample a second during the cycle. Alternatively, the valve leak frequency may be recorded at an intermittent sample rate during the cycle.

Embodiments of the present invention will now be described, by way of example only, and with references to the accompanying drawings, in which.

DIALYSIS MACHINE

Figure 1:
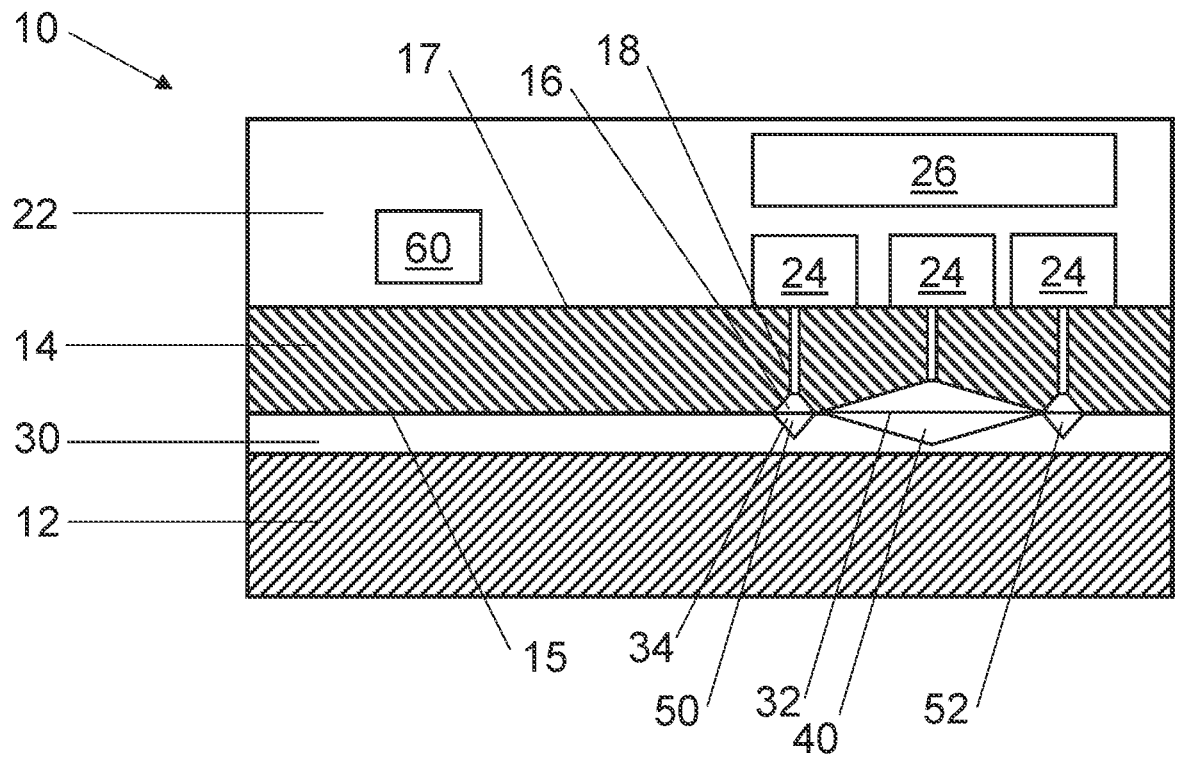
FIG. 1 is a schematic cross-sectional view of a dialysis machine.

A cross section of a dialysis machine 10 is shown schematically in FIG. 1. The dialysis machine 10 has machine body 22. The machine body 22 houses pneumatic actuators 24 and a controller 26. The dialysis machine 10 includes a first platen 12 and a second platen 14. The first and second platens 12, 14 together define a cavity into which a cartridge 30 is received in a known manner.

Figure 2:
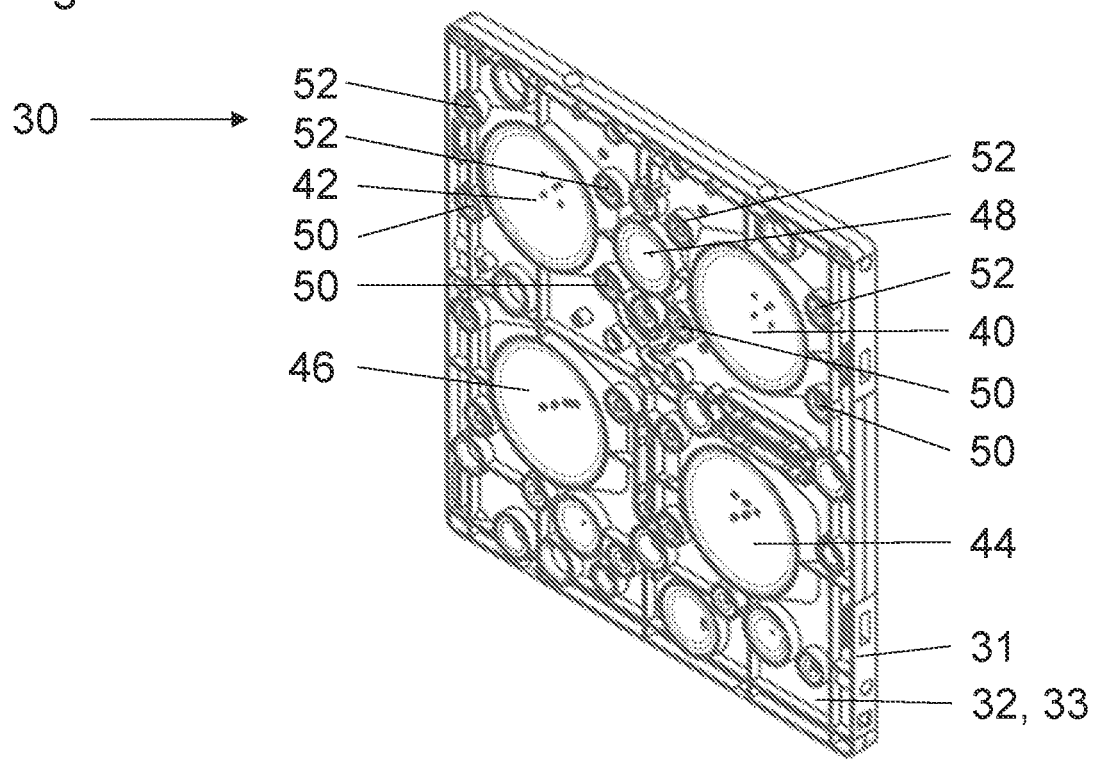
FIG. 2 is a perspective view of a cartridge of the dialysis machine of FIG. 1.
Figure 3:
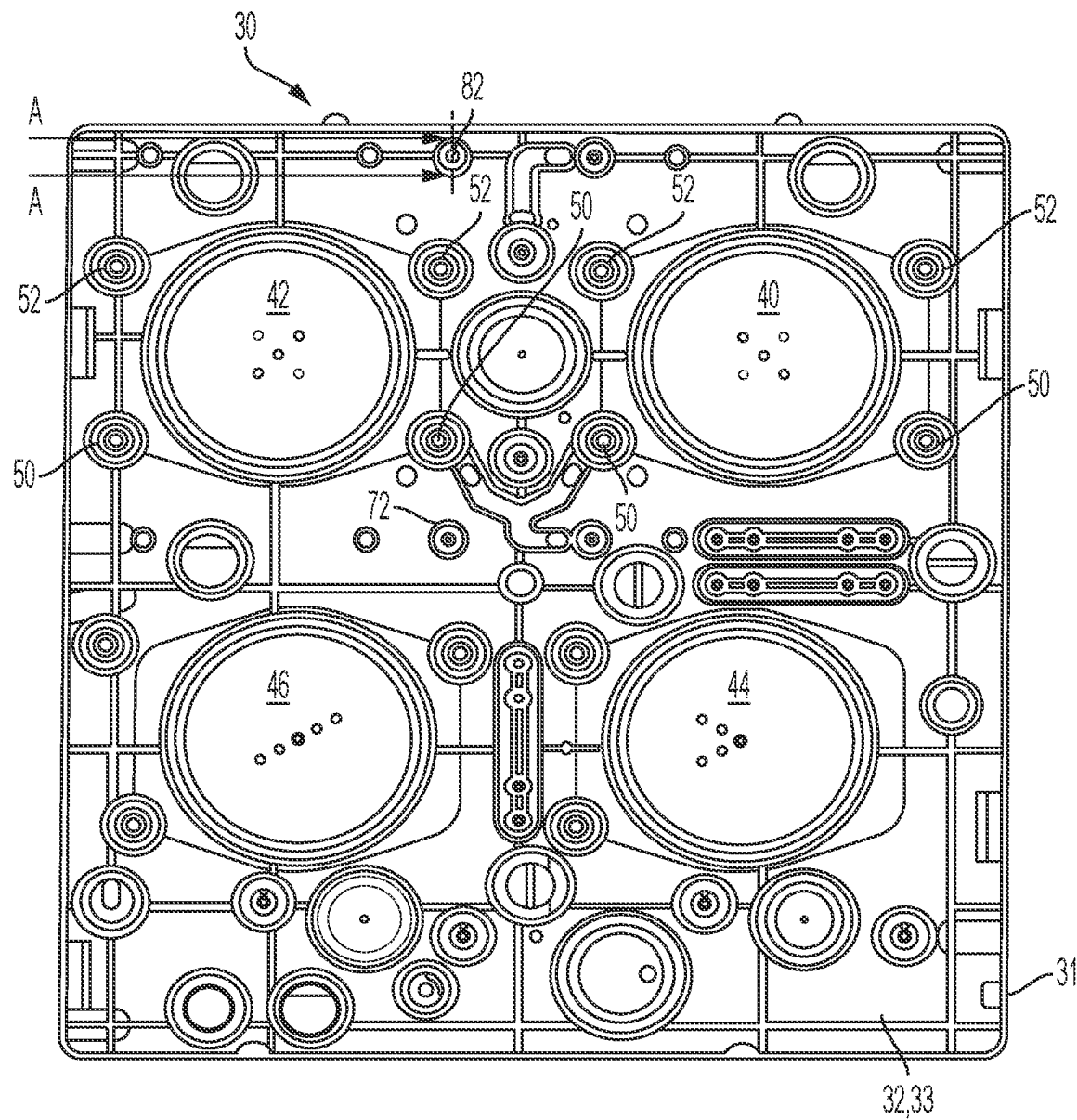
FIG. 3 is a plan view of the cartridge of FIG. 2.

The cartridge 30 (see FIGS. 2 and 3) has a rigid body 31 covered by a flexible membrane 32, providing a machine facing surface 33. The cartridge 30 in part embodies pump chambers and valves. In this case, the chambers are flow balance pump chamber "A" 40, flow balance pump chamber "B" 42, dialysate mixing pump chamber 44, acid mixing pump chamber 46 and ultrafiltration pump chamber 48. The flow balance pump chamber "A" 40 and flow balance pump chamber "B" 42 each have two inlet valves 50 and two outlet valves 52.

The pneumatic operation of each of the chambers 40, 42, 44, 46 and 48 are substantially similar, such that only the flow balance pump chamber "A" 40 shall be described in detail.

Furthermore, the two inlet valves 50 and the two outlet valves 52 are substantially similar, such that only one inlet valve 50 and one outlet valve 52 shall be described in detail.

Referring back to FIG. 1, the flow balance pump chamber "A" 40 and inlet and outlet valves 50, 52 are defined between respective concave cavities 34 formed in the rigid body 31 of the cartridge 30 and the flexible membrane of the cartridge 32. The cartridge 30 defines fluid pathways 28 between the flow balance pump chamber "A" 40 inlet and outlet valves 50, 52.

In use, the cartridge 30 is retained between the first platen 12 on a first side of the cartridge 30 and the second platen 14 on a second side of the cartridge 30. The second platen 14 has a cartridge engaging surface 15 and a non-cartridge engaging surface 17. Cavities 16 are defined within the cartridge engaging surface 15, which correspond to the concave cavities 34 on the cartridge 30. A fluid port 18 is defined in each of the concave cavities 16, fluidly connecting the cartridge engaging surface 15 and the non-cartridge engaging surface 17, of the second platen 14.

The pneumatic actuators 24 are arranged in fluid communication with the first side of the cartridge 30, through the second platen 14 via the fluid ports 18, and hence the machine facing surface 33 of the flexible membrane 32. The pump chambers and valves are operated pneumatically by actuating the flexible membrane 32 using the pneumatic actuators 24 provided in the machine body 22. In an alternative embodiment the pump chambers and valves are operated hydraulically.

Sensing Arrangement

Figure 4:
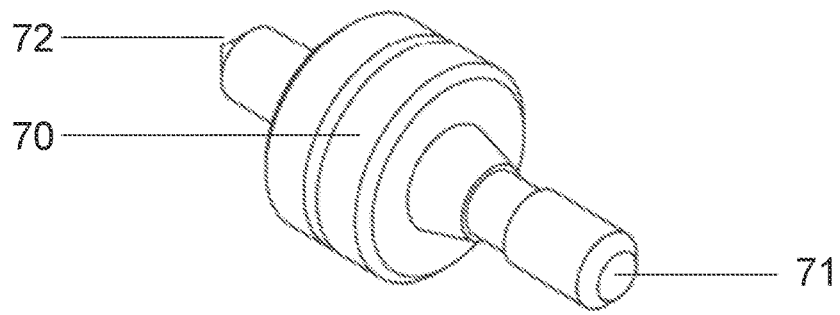
FIG. 4 is a perspective view of a sensing electrode.
Figure 5:
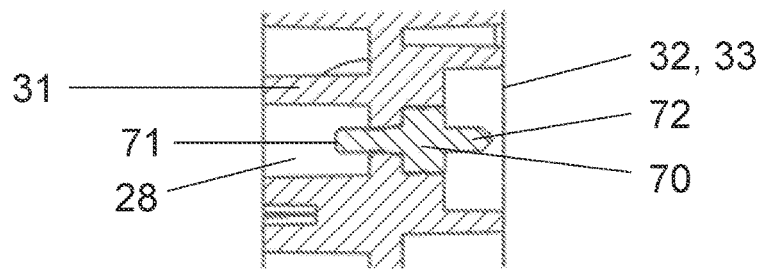
FIG. 5 is a partial cross-sectional view of the cartridge taken at line A-A of FIG. 3.

The pump chambers and valves are provided with sensing arrangements 60, each of which include two sensing electrodes, generally termed 70 (see FIGS. 4 and 5). The sensing electrodes 70 are rotationally symmetrical and are made of a conductive material. The sensing electrodes 70 include a pointed tip 71. The sensing electrodes 70 are mounted in the rigid body 31 of the cartridge 30. The pointed tip 71 is arranged to face the second side of the cartridge 30 and the flexible membrane 32.

Figure 6:
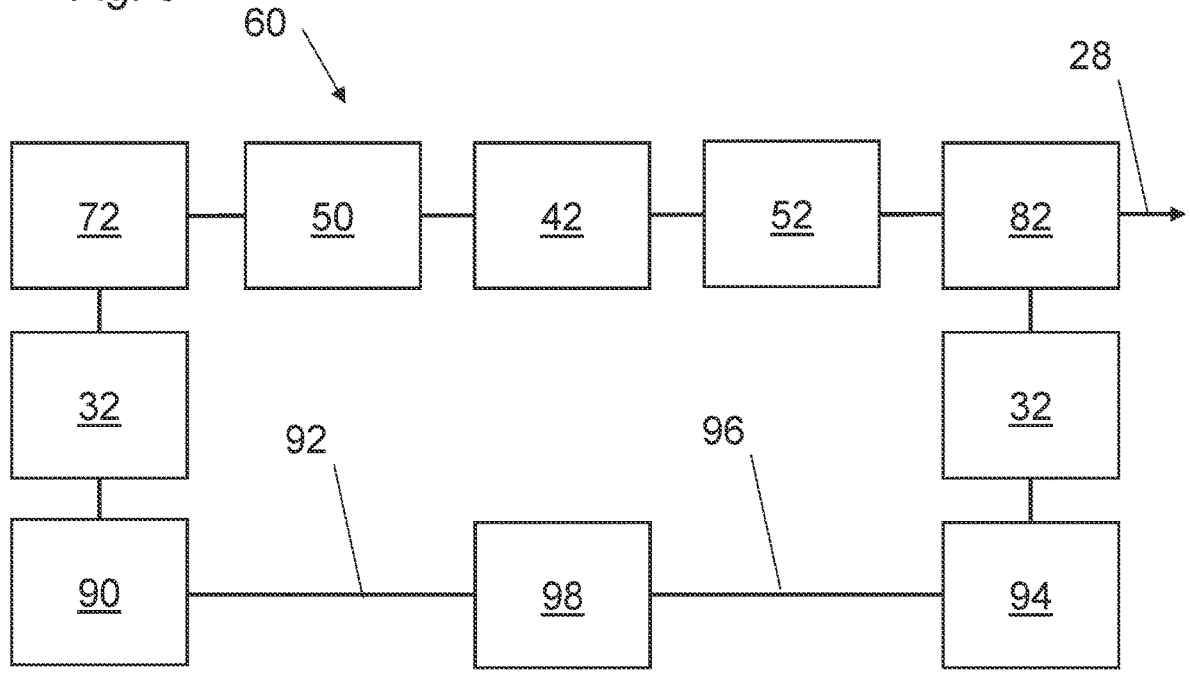
FIG. 6 is a schematic of the fluid flowpath of the sensing arrangement for flow balance pump "B".

The sensing arrangements 60 monitor the flow of fluids through the pump chambers and valves along the various fluid pathways. Referring to FIG. 6, one such fluid pathway is the fluid pathway 28 associated with the flow balance pump chamber "B" 42. As the sensing arrangements 60 are substantially similar, only the sensing arrangement 60 associated with the flow balance pump chamber "B" 42 shall be described in detail.

Flow Balance Pump Chamber "B" Sensing Arrangement

The flow balance pump chamber "B" sensing arrangement 60 is arranged with an inlet valve sensing electrode 72 and outlet valve sensing electrode 82. The inlet valve sensing electrode 72 is fixed to the rigid body 31 of the cartridge 30 with the pointed sensing tip 71 exposed to the fluid flowpath 28 at the entrance to the inlet valve 50. The outlet valve sensing electrode 82 is fixed to the rigid body 31 of the cartridge 30 with the pointed sensing tip 71 exposed to the fluid flowpath 28 at the exit of the outlet valve 52.

Thus the inlet valve sensing electrode 72 is provided upstream of the flow balance pump chamber "B" 42, and outlet valve sensing electrode 82 is provided downstream of the flow balance pump chamber "B" 42.

When the cartridge 30 is loaded into the dialysis machine 10, the inlet valve sensing electrode 72 and outlet valve sensing electrode 82 line up with sprung contacts 90, 94 provided in the second platen 14, sandwiching the flexible membrane 32 therebetween.

The sprung contacts 90, 94 are electrically connected to a processor 98, incorporating a sensor circuit, a comparator and a power source, provided in the machine body 22 via electrical connectors 92, 96 respectively.

Thus inlet valve sensing electrode 72 and outlet valve sensing electrode 82 are electrically connected to the processor 98 through the flexible membrane 32. The inlet valve sensing electrode 72 and outlet valve sensing electrode 82, together with the sprung contacts 90, 94, processor 98 and respective connectors 92, 96 form the sensing arrangement 60.

Valve Function

In use at least one of the inlet valve 50 and the outlet valve 52 will always be closed. That is, there are three modes of operation. In an idle mode, both the inlet valve 50 and the outlet valve 52 are closed. Thus there should be no continuous flowpath between the inlet valve sensing electrode 72 and the outlet valve sensing electrode 82.

In a fill mode, the inlet valve 50 is open, and the outlet valve 52 is closed. This allows flow balance pump chamber "B" to be filled. However, there should still be no continuous flowpath between the inlet valve sensing electrode 72 and the outlet valve sensing electrode 82, as the outlet valve is closed. In an empty mode, the inlet valve 50 is closed, and the outlet valve 52 is open. This allows flow balance pump chamber "B" to be emptied. However, there should still be no continuous flowpath between the inlet valve sensing electrode 72 and the outlet valve sensing electrode 82, as the inlet valve 50 is closed. Thus the valve leak system may detect when either of the inlet or outlet valves 50, 52 are leaking using the sensing arrangement 60 shown in FIG. 6.

Valve Leak Detection System, Using Sensing Arrangement

During operation of the dialysis machine 10, the sensing arrangements 60 are used to detect leakage across the pump chambers and valves of the Dialysis Machine.

The sensor circuit of the processor 98, includes an operational amplifier based relaxation oscillator whose frequency is determined by electrical conductance of the fluid path.

In use, an alternating potential difference from the power source is applied across the fluid flowpath 28 by the inlet valve sensing electrode 72. The conductance of the fluid flowpath 28 between the inlet valve 50 and outlet valve 52 of the flow balance pump chamber "B" 42 is measured at the outlet valve sensing electrode 82 by measuring the potential difference detected at the outlet valve sensing electrode 82, as will be described in more detail below. The potential differential provides an indication the conductivity of the fluid flowpath 28. The relaxation oscillator ensures that the sensing arrangement 60 operates with an alternating current with minimal direct current offset. This reduces the galvanic effects on the inlet valve sensing electrode 72 and the outlet valve sensing electrode 82.

The sensor circuit of the processor 98 generates the pulse train from the relaxation oscillator which is sent through the sensing arrangement 60, to output at the processor 98. The output at the processor is a series of pulses. From this series of pulses, a frequency is determined by measuring the time between the pulses, and hence fluid conductivity. This frequency value is known as the valve leak frequency.

The sensing arrangement 60 detects a valve leak in the inlet and outlet valves 50, 52 of the flow balance chamber "B" 42 by performing conductivity checks during operation of the flow balance system. The conductivity along a flow path should not exceed a defined limit if the flow path is interrupted by valves 50, 52. The test is performed once every pump operation. If the inlet or outlet valves 50, 52 fail to close, then the respective pump may draw or expel the fluid associated with that pump the wrong way, which is undesirable. The protective system for this error uses conductivity of the fluid flowpath 28 as a means to determine this failure. Thus in normal operation of the Dialysis Machine, there should never be a conductive path across the whole of the pump, from before the inlet valve 50 to after the outlet valve 52, that has a conductivity of a value equal to or greater than a limit value set by the particular geometry of the cartridge in question. If a conductive path is seen, this may be indicative of one of the valves 50, 52 having failed to close.

Hence the valve leak detection system measures a valve leak frequency value. The valve leak signal is generated by an oscillator and the frequency of the signal is determined by the feedback resistor. The sensing electrodes are connected in parallel to the feedback resistor so that a lower impedance across the valves would cause the total feedback resistor value to decrease, increasing the oscillating frequency.

During normal operation of an exemplary Dialysis Machine having an exemplary cartridge, the relaxation oscillator is tuned to generate a signal of 6 kHz for a resistance of 10 kOhms across the sensing electrodes. The expected detected valve leak frequency value is between 3 kHz and 4 kHz. Should a valve leak frequency value in excess of 6 kHz be detected, a valve leak has occurred.

Membrane Pump Usage Condition Detection

The valve leak detection system described above may be used to determine membrane pump usage and hence cartridge usage.

A partial valve leak (e.g. due to re-used cartridges) is detected when the variation of detected valve leak frequency value within a pumping cycle increases.

A variation in the detected valve leak frequency value is detected by the comparator within the processor 98 measuring the difference between the minimum and maximum valve leak frequency values measured within one pump cycle.

For the normal operation of an exemplary Dialysis Machine having an exemplary cartridge referred to above, variation of valve leak frequency value is between 200 Hz and 500 Hz. Variations above 1 kHz are considered to be partial valve leak. Thus for this exemplary Dialysis Machine having an exemplary cartridge, the pre-determined threshold value is a valve leak frequency value difference of 1 kHz.

The value used for the partial valve leak is not the absolute frequency but the variation of the frequency within a pumping cycle. When the valve is partially leaking (e.g. due to re-use of cartridges) the frequency signal is not as stable as it normally is: maximum relative difference of the valve leak frequency value within one pump cycle is more than 1 kHz. Normal expected values of absolute frequency are 3 kHz to 4 kHz with a variation of less than 1 kHz within a pumping cycle.

As the valve leak signal is generated by an oscillator and the frequency of the signal is determined by the feedback resistor, a dynamic threshold value for the valve leak frequency value difference may be used instead of the pre-determined threshold value.

The effects on a cartridge 30 during a dialysis treatment cycle can be represented by a typical test cycle. A typical test cycle includes three main stages, flow balance, ultrafiltration and purge. In the first 30 minutes, the dialysis machine 10 is taken through a flow balance stage of the test cycle. The flow balance stage tests the flow balance valves. During the next 30 minutes, the dialysis machine 10 is taken through an ultrafiltration stage of the test cycle. The ultrafiltration stage tests the ultrafiltration valves. The test cycle is then ended with a purge stage. The purge stage empties the cartridge 30 of all dialysate fluids, and cleans the fluid flow paths with reverse osmosis water.

In order to determine the deterioration rates, the same cartridge 30 is forced through repeated test cycles.

Valve Leak Frequency Profiles

Figure 7:
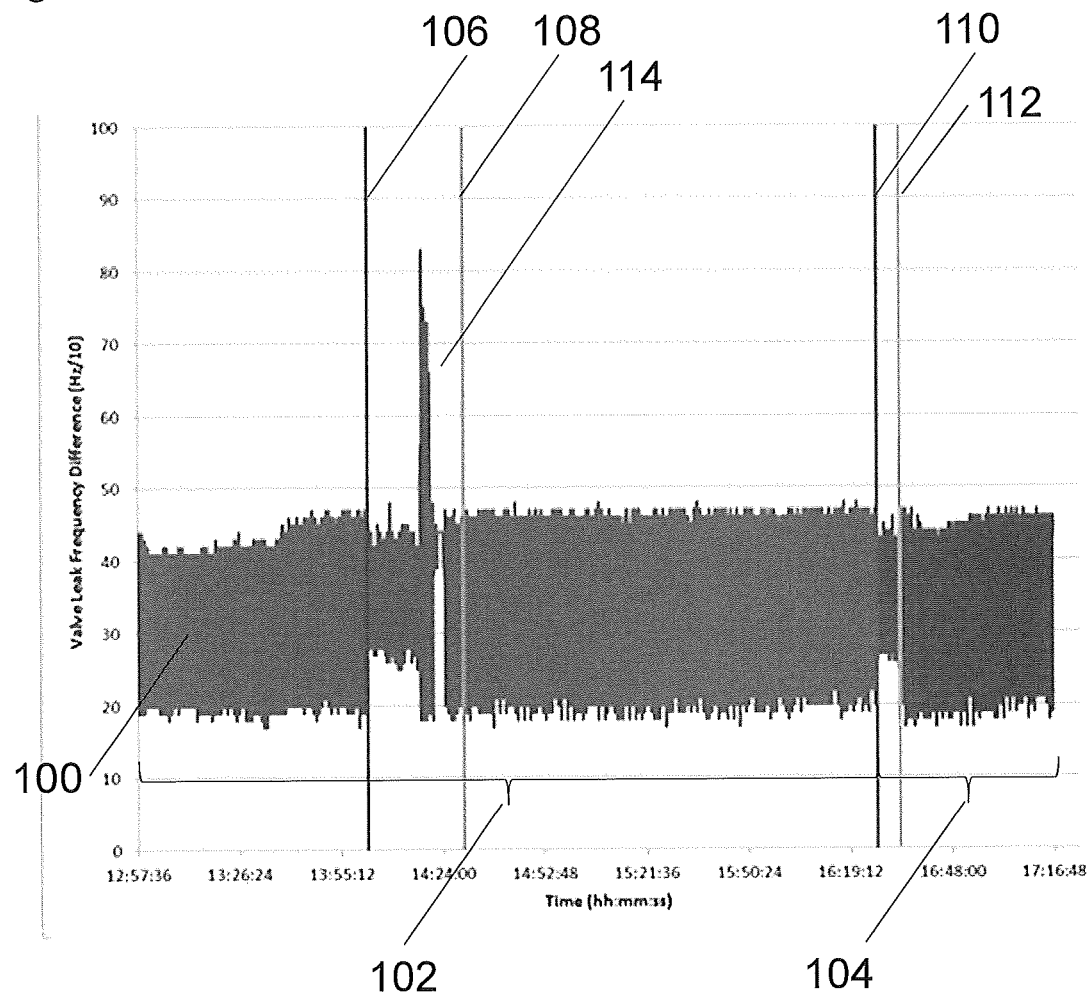
FIG. 7 is a valve leak detection frequency profile of a valve on a cartridge undergoing a typical cycle.

With reference to FIG. 7, a valve leak frequency profile between inlet valve 50 and outlet valve 52, i.e. the fluid flowpath 28 across the flow balance chamber "B" 42, on a cartridge 30 undergoing a typical cycle is shown. The valve leak frequency values are measured every second, a comparison is made between the minimum and maximum valve leak frequency values and plotted as point readings 100 with respect to the Y-axis. A general distribution over the typical cycle time as shown on the X-axis. The first stage of the typical cycle represents the ultrafiltration stage 102 of the cycle, whereas the second stage of the typical cycle represents the flow balance stage 104 of the cycle. During ultrafiltration the blood pump is stopped at 106 and re-started at 108. Similarly, during flow balance, the blood pump is stopper at 110 and re-started at 112.

As can be seen in FIG. 7, whilst the measured valve leak frequency difference varies during a normal treatment session, the magnitude of any single difference value 100 does not exceed 900 Hz. The typical value throughout the cycle for valve leak frequency difference is between 200 Hz and 500 Hz. A spike 114 in the measured valve leak frequency difference value is seen during the ultrafiltration stage 102 of the cycle, the spike 114 reaching a maximum value of approximately 830 Hz.

Figure 8:
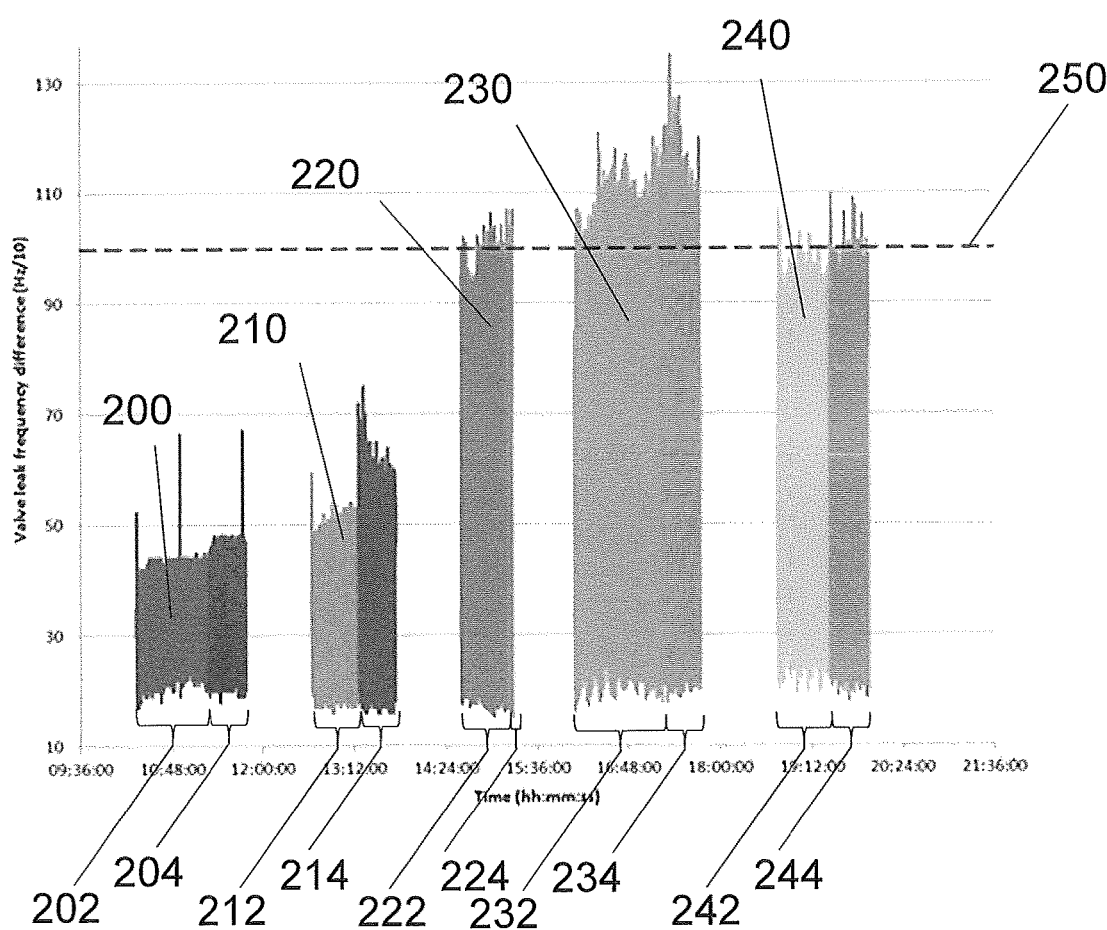
FIG. 8 is a valve leak detection frequency profile of a valve on a cartridge undergoing a sequence of cycles.

With reference to FIG. 8, a cartridge 30 is taken through a series of five typical cycles, numbered as first cycle 200, second cycle 210, third cycle 220, fourth cycle 230 and fifth cycle 240. For each cycle, the valve leak frequency difference values are again plotted as point readings with respect to the Y-axis giving a general distribution over the typical cycle time as shown on the X-axis. Each cycle 200, 210, 220, 230, 240 includes an ultrafiltration stage 202, 212, 222, 232, 242, a flow balance stage 204, 214, 224, 234, 244, and a purge stage. The purge stage follows the flow balance stage 204, 214, 224, 234, 244 for each of the cycles 200, 210, 220, 230, 240 respectively.

The valve leak frequency difference limit 250 is shown as a dashed line at 1000 Hz. The valve leak frequency difference limit 250 may be manipulated depending on the deterioration rates displayed by the cartridge 30.

An increase in the valve leak frequency difference values can be seen from the first cycle 200 to the second cycle 210. This increase in the valve leak frequency difference value represents a deterioration in the flexible membrane of the cartridge. A yet greater increase in the valve leak frequency difference values is seen from the second cycle 210 to the third cycle 220. An alarm is raised during the third cycle 220, as the point readings regularly breach the 1000 Hz valve leak frequency difference limit 250.

Thus FIG. 8 shows that the valve leak frequency difference values increase over several cycles with the method described above, with the rate of deterioration being worse after each re-use, until the flexible membrane is effectively plastically deformed. Further re-use of the same cartridge will thus prevent meaningful treatment sessions, as evidenced in the fourth and fifth cycles 230, 240.

Figure 9:
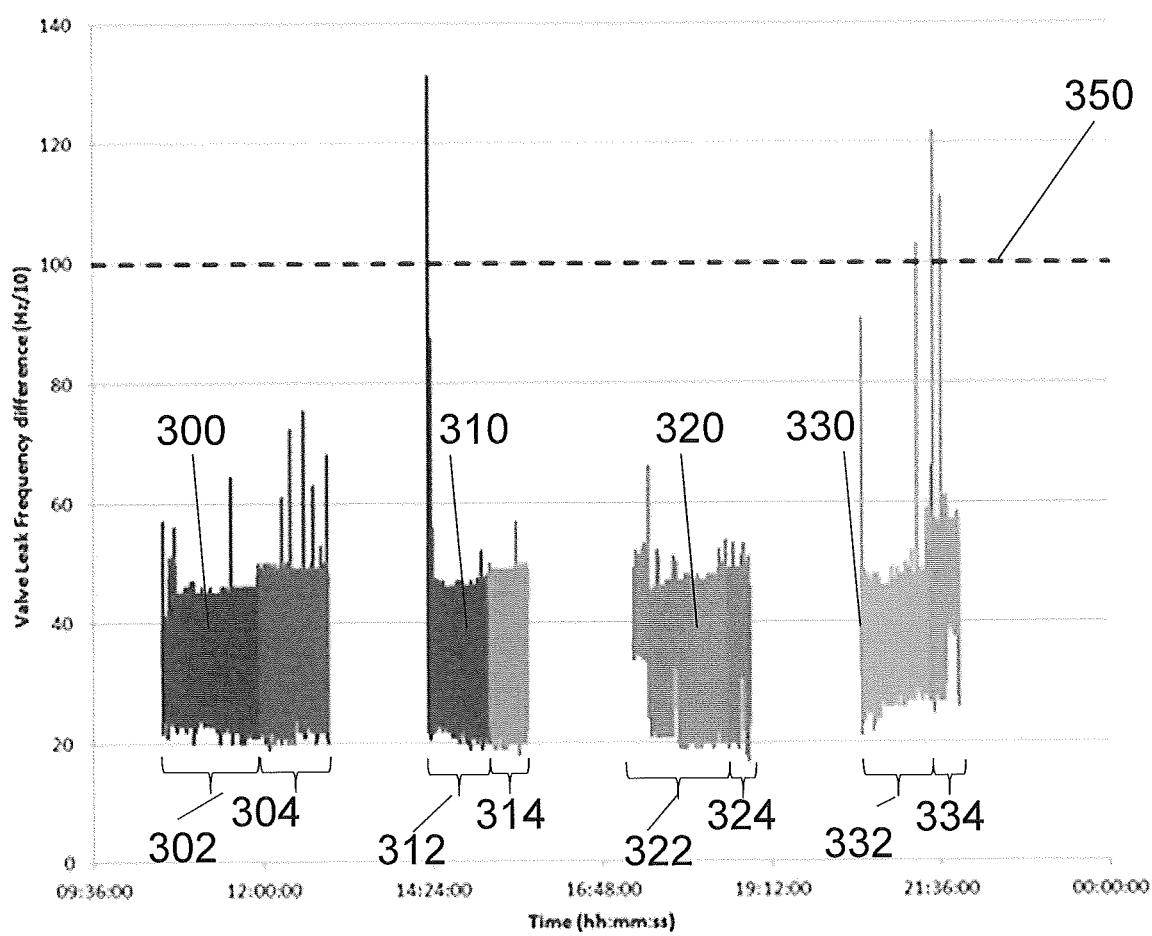
FIG. 9 is a valve leak detection frequency profile of a valve on a cartridge undergoing a sequence of cycles, each cycles omitting the purging stage.

With reference to FIG. 9, a cartridge 30 is taken through a series of five typical cycles, numbered as first cycle 300, second cycle 310, third cycle 320 and fourth cycle 330. For each cycle, the valve leak frequency difference values are again plotted as point readings with respect to the Y-axis giving a general distribution over the typical cycle time as shown on the X-axis. Each cycle 300, 310, 320, 330 includes an ultrafiltration stage 302, 312, 322, 332, and a flow balance stage 304, 314, 324, 334, respectively, however, unlike in FIG. 8, no purge stage. Instead, the dialysis machine 10 is switched off just before the purge stage.

The valve leak frequency difference limit 350 is shown as a dashed line at 1000 Hz.

FIG. 9 shows that the degree of cartridge 30 deterioration is minimal if the purge stage is avoided, thereby allowing an alternative method to re-use the cartridge if necessary. This method of ageing the cartridge 30 does not appear to cause any noticeable deterioration.

Thus the method of determining a cartridge usage condition records the valve leak frequency during the cycle to obtain a characteristic value, and determines the cartridge usage condition based on the characteristic value. The characteristic value may be a single breach of the 1000 Hz valve leak frequency difference limit 250. The characteristic value may be a discreet number of breaches of the 1000 Hz valve leak frequency difference limit 250. The characteristic value may be a decay rate of the valve leak frequency difference following a spike in the valve leak frequency difference. The characteristic value may be the mean, median or modal average valve leak frequency difference during the cycle. The processor 98 may be programmed to monitor any of the preceding characteristic values. On receipt of a characteristic value, the process may send a signal to a graphical user interface, or to an audible or visual alarm to indicate the cartridge usage condition or a signal to prevent activation of the dialysis machine cycle.

Thus the detection system is sensitive enough so that it detects a deterioration of the cartridge membrane before a leak across the valve is established. This allows an operator to prevent use of a cartridge not fit for purpose.

Although the valve leak frequency is described as being measured using the sensing arrangements including sensing electrodes, other sensing arrangements are envisaged. A capacitance probe, which provides a non-contacting fluid flowpath sensing arrangement, is also envisaged, as is an inductance probe which is non-contacting. Other relaxation oscillator types may be used, such as a transistor based relaxation oscillator.

The invention claimed is:

1. A system for detecting a usage condition of a membrane pump, the system comprising:
    a cartridge including a rigid body and a deformable membrane, the rigid body and the deformable membrane together defining at least a portion of the membrane pump including a chamber and at least one valve in fluid communication with one another along a flow path defined by the cartridge, the at least one valve operable to open and close the flow path extending through the chamber of the membrane pump;
    a measuring device;
    a comparator;
    a signal generator, wherein:
        the measuring device is configured to determine a value of an electrical characteristic between two points on the flow path of the cartridge, a first point on the flow path upstream of the at least one valve and a second point on the flow path downstream of the at least one valve,
        the measuring device measures the value of the electrical characteristic when the at least one valve is closed,
        the comparator is configured to monitor the value of the electrical characteristic, and
        the signal generator is arranged to provide an output signal, corresponding to the usage condition of the membrane pump, when the value of the electrical characteristic is indicative of deterioration of the membrane pump; and
    a processor arranged to receive the output signal comprising an error message for prevention of further use of the cartridge.

2. The system according to claim 1, wherein the electrical characteristic is one of conductance, impedance or capacitance.

3. The system according to claim 1, wherein the output signal is stored in the processor.

4. A system for detecting a usage condition of a membrane pump the system comprising:
    a cartridge including a rigid body and a deformable membrane, the rigid body and the deformable membrane together defining at least a portion of the membrane pump including a chamber and at least one valve in fluid communication along a flow path defined by the cartridge, the at least one valve operable to open and close the flow path extending through the chamber of the membrane pump;
    a measuring device;
    a comparator;
    a signal generator, wherein:
        the measuring device is configured to determine a value of an electrical characteristic between two points on the flow path of the cartridge, a first point on the flow path arranged upstream of the at least one valve and a second point on the flow path arranged downstream of the at least one valve,
        the measuring device measures the value of the electrical characteristic when the at least one valve is closed,
        the comparator is configured to monitor the value of the electrical characteristic, and
        the signal generator is arranged to provide an output signal, corresponding to the usage condition of the membrane pump, when the value of the electrical characteristic is indicative of deterioration of the membrane pump;
    and
    a processor arranged to receive the output signal, wherein the processor calculates a specific number of uses of the cartridge from the value of the electrical characteristic indicative of the deterioration of the membrane pump.

5. The system according to claim 1, wherein the comparator compares the value of the electrical characteristic with a pre-determined threshold value thereof.

6. The system according to claim 5, wherein the output signal is provided when the value of the electrical characteristic is above the pre-determined threshold value or falls below the pre-determined threshold value.

7. A system for detecting a usage condition of a membrane pump, the system comprising:
    a cartridge including a rigid body and a deformable membrane, the rigid body and the deformable membrane together defining at least a portion of the membrane pump including a chamber and at least one valve in fluid communication with one another along a flow path defined by the cartridge, the at least one valve operable to open and close the flow path extending through the chamber of the membrane pump;
a measuring device;
a comparator;
a signal generator, wherein:
the measuring device is configured to determine a value of an electrical characteristic between two points on the flow path of the cartridge, a first point on the flow path upstream of the at least one valve and a second point on the flow path downstream of the at least one valve,
the measuring device measures the value of the electrical characteristic when the at least one valve is closed,
the comparator is configured to monitor the value of the electrical characteristic, and
the signal generator is arranged to provide an output signal, corresponding to the usage condition of the membrane pump, when the value of the electrical characteristic is indicative of deterioration of the membrane pump;
and
a processor arranged to permit a set number of re uses of the cartridge based on the output signal.

8. The system according to claim 1, wherein the measuring device includes a pair of electrodes or a pair of capacitance probes.

9. A method of determining a usage condition of a membrane pump, the method comprising the steps of:
providing a dialysis machine including a cartridge, a measuring device, a comparator, and a signal generator, the cartridge having a rigid body and a deformable membrane, the rigid body and the deformable membrane together defining at least a portion of the membrane pump including a chamber and at least one valve in fluid communication with one another along a flow path defined by the cartridge, the at least one valve operable to open and close the flow path extending through the chamber of the membrane pump;
configuring the measuring device for determining a value of an electrical characteristic between two points on the flow path of the cartridge, a first point on the flow path upstream of the at least one valve and a second point on the flow path downstream of the at least one valve;
operating the dialysis machine through a cycle;
with the at least one valve closed, measuring the value of the electrical characteristic;
monitoring the value of the electrical characteristic throughout the cycle using the comparator;
and
providing an output signal, corresponding to the usage condition of the membrane pump, when the value of the electrical characteristic is indicative of deterioration of the membrane pump, wherein the output signal comprises an error message for prevention of further use of the cartridge.

10. The method according to claim 9, wherein the electrical characteristic is one of conductance, impedance or capacitance.

11. The method according to claim 9, wherein:
the step of monitoring the value of the electrical characteristic includes recording the value of the electrical characteristic upon the value being above a limit value, or recording a series of values of the electrical characteristic above a limit value,
or
a recording a decay rate of a leak frequency difference of the at least one valve following a spike in the valve frequency difference of the at least one valve, and the decay rate is indicative of a specific number of uses of the cartridge.

12. The method according to claim 9, wherein:
the value of the electrical characteristic is a decay rate of a valve difference in leak frequency of the at least one valve following a spike in the difference in leak frequency of the at least one valve, and the decay rate is indicative of a specific number of uses of the cartridge,
or
the value of the electrical characteristic is a mean, median or modal average of the difference in leak frequency of the at least one valve during the cycle.

13. The method according to claim 9, wherein a valve leak frequency is recorded at a sample rate of 1 sample per second during the cycle.

14. The method according to claim 9, wherein a valve leak frequency is recorded at an intermittent sample rate during the cycle.

15. A dialysis machine comprising the system according to claim 1.

16. A method of determining a usage condition of a membrane pump, the method comprising the steps of:
providing a dialysis machine including a cartridge, a measuring device, a comparator, and a signal generator, the cartridge having a rigid body and a deformable membrane, the rigid body and the deformable membrane together defining at least a portion of the membrane pump including a chamber and at least one valve in fluid communication with one another along a flow path defined by the cartridge, the at least one valve operable to open and close the flow path extending through the chamber of the membrane pump;
configuring the measuring device for determining a value of an electrical characteristic between two points on the flow path of the cartridge, a first point on the flow path upstream of the at least one valve and a second point on the flow path downstream of the at least one valve;
operating the dialysis machine through a cycle;
with the at least one valve closed, measuring the value of the electrical characteristic;
monitoring the value of the electrical characteristic throughout the cycle using the comparator;
providing an output signal, corresponding to the usage condition of the membrane pump, when the value of the electrical characteristic is indicative of deterioration of the membrane pump;
and
based on the value of the electrical characteristic, calculating a specific number of uses of the cartridge.

17. The system of claim 1, wherein the error message prevents activation of a cycle of a dialysis machine into which the cartridge is inserted.

* * * * *